United States Patent
Mann et al.

(10) Patent No.: US 6,809,653 B1
(45) Date of Patent: Oct. 26, 2004

(54) TELEMETERED CHARACTERISTIC MONITOR SYSTEM AND METHOD OF USING THE SAME

(75) Inventors: Alfred E. Mann, Beverly Hills, CA (US); Richard E. Purvis, Pasadena, CA (US); John J. Mastrototaro, Los Angeles, CA (US); James D. Causey, Simi Valley, CA (US); James Henke, Simi Valley, CA (US); Peter Hong, Santa Clarita, CA (US); John H. Livingston, Newport Beach, CA (US); Clifford W. Hague, Sherman Oaks, CA (US); Brad T. Hite, Valencia, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 09/465,715

(22) Filed: Dec. 17, 1999

Related U.S. Application Data

(63) Continuation of application No. 09/377,472, filed on Aug. 19, 1999.
(60) Provisional application No. 60/103,812, filed on Oct. 8, 1998.

(51) Int. Cl.[7] ............................................. A61M 5/00
(52) U.S. Cl. .................. 340/870.28; 604/31; 604/506
(58) Field of Search .......................... 604/31, 506, 174; 600/316, 347, 508; 607/57; 439/67; 128/899; 340/870.28

(56) References Cited

U.S. PATENT DOCUMENTS 4,494,950 A   1/1985   Fischell
4,703,756 A   11/1987  Gough et al.
4,871,351 A   10/1989  Feingold
4,935,105 A   6/1990   Churchouse ............ 204/153.12

(List continued on next page.)

FOREIGN PATENT DOCUMENTS

| EP | 0098592 | 1/1984 |
|---|---|---|
| EP | 0680727 | 11/1995 |
| WO | 9528878 | 11/1995 |
| WO | 9856293 | 12/1998 |
| WO | 9945375 | 9/1999 |
| WO | 9945387 | 9/1999 |
| WO | 9956613 | 11/1999 |

Primary Examiner—Michael Horabick
Assistant Examiner—Hung Dang
(74) Attorney, Agent, or Firm—Medtronic MiniMed, Inc.

(57) ABSTRACT

A telemetered characteristic monitor system includes a remotely located data receiving device, a sensor for producing signal indicative of a characteristic of a user, and a transmitter device. The transmitter device includes a housing, a sensor connector, a processor, and a transmitter. The transmitter receives the signals from the sensor and wirelessly transmits the processed signals to the remotely located data receiving device. The processor coupled to the sensor processes the signals from the sensor for transmission to the remotely located data receiving device. The data receiving device may be a characteristic monitor, a data receiver that provides data to another device, an RF programmer for a medical device, a medication delivery device (such as an infusion pump), or the like.

5 Claims, 5 Drawing Sheets

U.S. PATENT DOCUMENTS

| | | | |
|---|---|---|---|
| 4,953,552 A | 9/1990 | DeMarzo | |
| 5,108,819 A | 4/1992 | Heller et al. | 428/195 |
| 5,113,869 A * | 5/1992 | Nappholz et al. | 600/508 |
| 5,376,070 A * | 12/1994 | Purvis et al. | 604/31 |
| 5,390,671 A * | 2/1995 | Lord et al. | 600/347 |
| 5,391,250 A | 2/1995 | Cheney, II et al. | 156/268 |
| 5,411,647 A | 5/1995 | Johnson et al. | 204/153.1 |
| 5,417,222 A | 5/1995 | Dempsey et al. | |
| 5,482,473 A * | 1/1996 | Lord et al. | 439/67 |
| 5,507,288 A | 4/1996 | Bocker et al. | |
| 5,545,191 A * | 8/1996 | Mann et al. | 607/57 |
| 5,558,640 A | 9/1996 | Pfeiler et al. | |
| 5,586,553 A * | 12/1996 | Halili et al. | 600/316 |
| 5,777,060 A | 7/1998 | Van Antwerp | 528/28 |
| 5,779,665 A * | 7/1998 | Mastrototaro et al. | 605/506 |
| 5,786,439 A | 7/1998 | Van Antwerp et al. | 528/77 |
| 5,791,344 A * | 8/1998 | Schulman et al. | 600/347 |
| 5,925,021 A | 7/1999 | Castellano et al. | |
| 5,951,521 A * | 9/1999 | Mastrototaro et al. | 604/174 |
| 5,965,380 A | 10/1999 | Heller et al. | 435/14 |
| 6,067,474 A * | 5/2000 | Schulman et al. | 607/57 |
| 6,175,752 B1 | 1/2001 | Say et al. | |
| 6,248,067 B1 | 6/2001 | Causey et al. | |
| 6,250,309 B1 * | 6/2001 | Krichen et al. | 128/899 |
| 6,254,586 B1 * | 7/2001 | Mann et al. | 604/506 |

\* cited by examiner

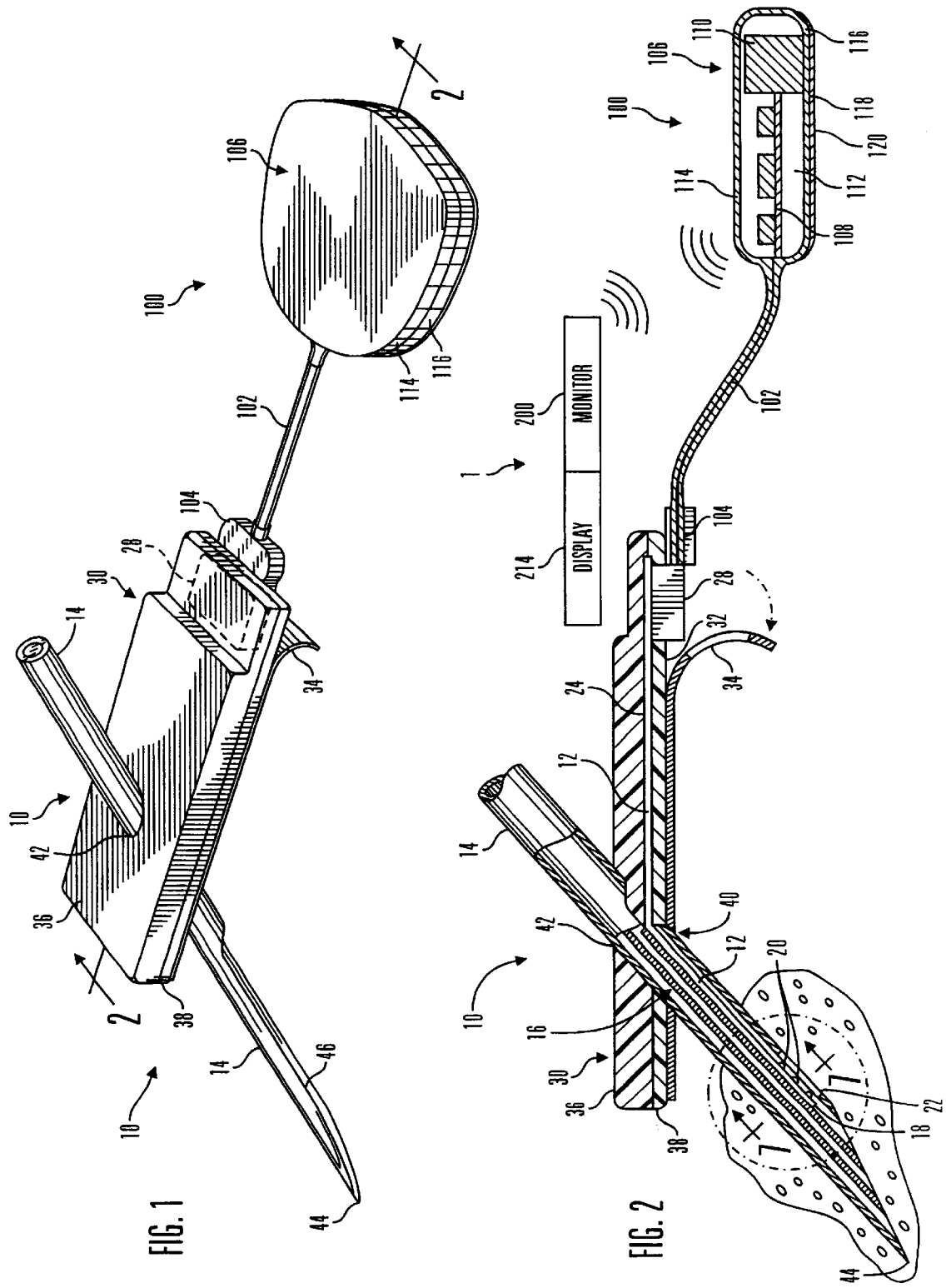

TELEMETERED CHARACTERISTIC MONITOR SYSTEM AND METHOD OF USING THE SAME

RELATED APPLICATIONS

This application is a continuation of Ser. No. 09/377,472 filed Aug. 19, 1999.

This application claims priority on U.S. Provisional Application Ser. No. 60/103,812 filed on Oct. 8, 1998, which is specifically incorporated by reference herein.

FIELD OF THE INVENTION

This invention relates to telemetered subcutaneous sensor devices and, in particular embodiments, to devices and methods for wireless communication between an implantable subcutaneous sensor set at a selected insertion site within the body of a user and a remotely located characteristic monitor.

BACKGROUND OF THE INVENTION

Over the years, a variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678, 408; and 4,685,903; or automated implantable medication infusion pumps, as generally described in U.S. Pat. No. 4,573,994, which are herein incorporated by reference.

Generally, small and flexible electrochemical sensors can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's interstitial fluid, blood, or the like, and a corresponding exposed plurality of conductive contacts at another end for convenient external electrical connection with a suitable monitoring device through a wire or cable. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

Drawbacks to the use of implantable sensors arise from the use of a wired connection between the implantable sensor set and the monitor. The use of the wire or cable is an additional inconvenience to users that already utilize an external infusion pump that includes an infusion insertion set and tube to infuse the medication. Also, the preferred site for some sensing device may be inconvenient for connection by wire to a characteristic monitor. For implantable pumps, the wire or cable negates the very benefit of having an internal device without external wires or cables. For Type 2 diabetics, who do not necessarily need or use an infusion pump, the use of a cable is seen as an inconvenience that may inhibit use of the device. In addition, the use of a wire or cable limits a user's ability to position the monitor, since it can be placed no further away than the ultimate length of the wire or cable. Thus, the user must normally wear the monitor, which can be problematic. For example, removal of the monitor for sleeping can be difficult, since a user would tend to become "tangled" in the wire or cable, between the sensor and the monitor, during the normal tossing and turning that occurs during sleep. Furthermore, the more connections the user must deal with (e.g., infusion pump and catheter and/or monitor with wire to sensor), the more complicated it is to use the devices, and the less likely the user will maintain compliance with the medical regimen due to perceived and actual difficulties with all of the wires and cables.

SUMMARY OF THE DISCLOSURE

It is an object of an embodiment of the present invention to provide an improved telemetered implantable sensor set (such as a subcutaneous or percutaneous sensor) and monitor connection device, which obviates for practical purposes, the above mentioned limitations.

According to an embodiment of the invention, a telemetered characteristic monitor system includes a remotely located data receiving device, a sensor for producing signal indicative of a characteristic of a user, and a transmitter device. In preferred embodiments, the transmitter device includes a housing, a sensor connector, a processor, and a transmitter. A potentiostat within the transmitter device may be coupled to the sensor connector and applies power to the sensor. The sensor connector receives the produced signals from the sensor. The processor is coupled to the sensor connector and processes the signals from the sensor for delivery to the remotely located data receiving device. The transmitter is coupled to the processor for wirelessly transmitting the processed signals to the remotely located data receiving device. In preferred embodiments, the data receiving device is a characteristic monitor. However, in other embodiments, the data receiving device is a data receiver that provides data to another device, an RF programmer, a medication delivery device (such as an infusion pump), or the like.

In particular embodiments, the transmitter of the transmitter device transmits the processed signals by radio frequencies. In other embodiments, the sensor may be implanted in and/or through subcutaneous, dermal, subdermal, intra-peritoneal or peritoneal tissue, and the sensor connector of the transmitter device includes a cable that is connected to the sensor. Also, the implantable sensor can be configured for a wired connection to a characteristic monitor, and the sensor connector of the transmitter device is formed to connect to the configured implantable sensor. Still further embodiments of the transmitter device include a receiver to receive data and instructions from the characteristic monitor, or the like.

Embodiments of the transmitter device (when used with a subcutaneous or percutaneous sensor) may include a biocompatible adhesive to secure the housing to a skin surface of the user. Preferably, the housing of the transmitter device is less than about 3.0 inches in diameter by 0.5 inches thick. In addition, the housing is resistant to fluids when immersed in a fluid, operable in a temperature range of 0° C. to 50° C., and has an operable life of at least 3 months. If the sensor is fully implanted, the transmitter that is connected to the sensor may be secured by sutures, sewing rings, or the like.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 1 is a perspective view illustrating a subcutaneous sensor insertion set and telemetered characteristic monitor transmitter device embodying the novel features of the invention;

FIG. 2 is an enlarged longitudinal vertical section taken generally on the line 2-2 of FIG. 1;

DETAILED DESCRIPTION OF THE PREFERRED EMBODIMENTS

Figure 3:
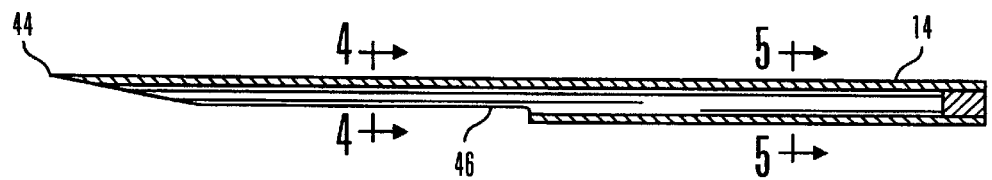
FIG. 3 is an enlarged longitudinal sectional of a slotted insertion needle used in the insertion set of FIGS. 1 and 2.
Figure 4:
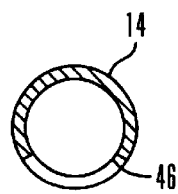
FIG. 4 is an enlarged transverse section taken generally on the line 4-4 of FIG. 3.
Figure 5:
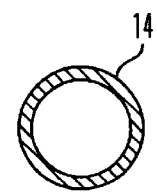
FIG. 5 is an enlarged transverse section taken generally on the line 5-5 of FIG. 3.

As shown in the drawings for purposes of illustration, the invention is embodied in a telemetered characteristic monitor transmitter coupled to a sensor set, that may be implanted in and/or through subcutaneous, dermal, sub-dermal, inter-peritoneal or peritoneal tissue, that transmits data from the sensor set to the characteristic monitor for determining body characteristics. In preferred embodiments of the present invention, the sensor set and monitor are for determining glucose levels in the blood and/or body fluids of the user without the use of, or necessity of, a wire or cable connection between the transmitter and the monitor. However, it will be recognized that further embodiments of the invention may be used to determine the levels of other agents, characteristics or compositions, such as hormones, cholesterol, medication concentrations, pH, oxygen saturation, viral loads (e.g., HIV), or the like. In other embodiments, the sensor set may also include the capability to be programmed or calibrated using data received by the telemetered characteristic monitor transmitter device, or may be calibrated at the monitor device (or receiver). The telemetered characteristic monitor system is primarily adapted for use in subcutaneous human tissue. However, still further embodiments may be placed in other types of tissue, such as muscle, lymph, organ tissue, veins, arteries or the like, and used in animal tissue. Embodiments may provide sensor readings on an intermittent or continuous basis.

The telemetered characteristic monitor system 1, in accordance with a preferred embodiment of the present invention include a percutaneous sensor set 10, a telemetered characteristic monitor transmitter device 100 and a characteristic monitor 200. The percutaneous sensor set 10 utilizes an electrode-type sensor, as described in more detail below. However, in alternative embodiments, the system may use other types of sensors, such as chemical based, optical based or the like. In further alternative embodiments, the sensors may be of a type that is used on the external surface of the skin or placed below the skin layer of the user. Preferred embodiments of a surface mounted sensor would utilize interstitial fluid harvested from underneath the skin. The telemetered characteristic monitor transmitter 100 generally includes the capability to transmit data. However, in alternative embodiments, the telemetered characteristic monitor transmitter 100 may include a receiver, or the like, to facilitate two-way communication between the sensor set 10 and the characteristic monitor 200. The characteristic monitor 200 utilizes the transmitted data to determine the characteristic reading. However, in alternative embodiments, the characteristic monitor 200 may be replaced with a data receiver, storage and/or transmitting device for later processing of the transmitted data or programming of the telemetered characteristic monitor transmitter 100.

Figure 13:
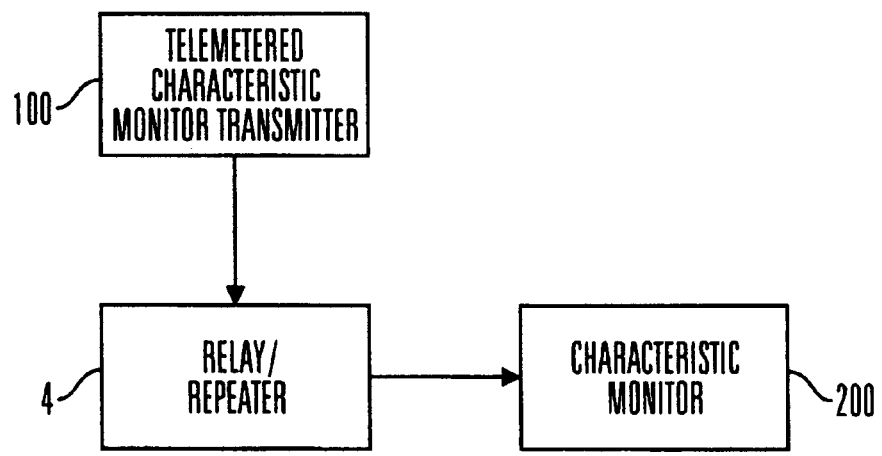
FIG. 13 is a simplified block diagram of a telemetered characteristic monitor transmitter and sensor set system in accordance with another embodiment of the present invention.
Figure 14:
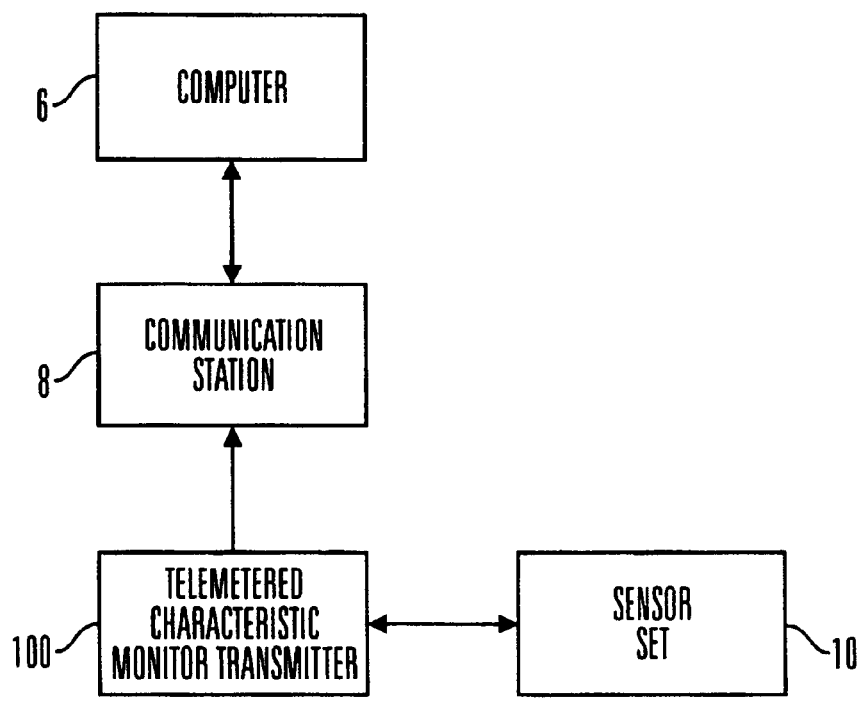
FIG. 14 is a simplified block diagram of a telemetered characteristic monitor transmitter and characteristic monitor system in accordance with still another embodiment of the present invention.

In addition, a relay or repeater 4 may be used with a telemetered characteristic monitor transmitter 100 and a characteristic monitor 200 to increase the distance that the telemetered characteristic monitor transmitter 100 can be used with the characteristic monitor 200, as shown in FIG. 13. For example, the relay 4 could be used to provide information to parents of children using the telemetered characteristic monitor transmitter 100 and the sensor set 10 from a distance. The information could be used when children are in another room during sleep or doing activities in a location remote from the parents. In further embodiments, the relay 4 can include the capability to sound an alarm. In addition, the relay 4 may be capable of providing telemetered characteristic monitor transmitter 100 data from the sensor set 10, as well as other data, to a remotely located individual via a modem connected to the relay 4 for display on a monitor, pager or the like. The data may also be downloaded through a Communication-Station 8 to a remotely located computer 6 such as a PC, lap top, or the like, over communication lines, by modem or wireless connection, as shown in FIG. 14. Also, some embodiments may omit the Communication Station 8 and uses a direct modem or wireless connection to the computer 6. In further embodiments, the telemetered characteristic monitor transmitter 100 transmits to an RF programmer, which acts as a relay, or shuttle, for data transmission between the sensor set 10 and a PC, laptop, Communication-station, a data processor, or the like. In further alternatives, the telemetered characteristic monitor transmitter 100 may transmit an alarm to a remotely located device, such as a communication-station, modem or the like to summon help. In addition, further embodiments may include the capability for simultaneous monitoring of multiple sensors and/or include a sensor for multiple measurements.

Still further embodiments of the telemetered characteristic monitor transmitter 100 may have and use an input port for direct (e.g., wired) connection to a programming or data readout device and/or be used for calibration of the sensor set 10. Preferably, any port would be water proof (or water resistant) or include a water proof, or water resistant, removable cover.

The purpose of the telemetered characteristic monitor system 1 (see FIG. 2) is to provide for better treatment and control in an outpatient or a home use environment. For example, the monitor system 1 can provide indications of glucose levels, a hypoglycemia/hyperglycemia alert and outpatient diagnostics. It is also useful as an evaluation tool under a physician's supervision.

The monitor system 1 also removes inconvenience by separating the monitor electronics into two separate devices; a telemetered characteristic monitor transmitter 100, which attaches to the implantable sensor set 10; and a characteristic monitor 200 (or other receiver), which is carried like a pager. This provides several advantages over wire connected devices. For instance, the user can more easily conceal the presence of the monitor system 1, since a wire will not be visible (or cumbersome), within clothing. Such remote communication also provides greater convenience and flexibility in the placement of the sensor. It also makes it is easier to protect the characteristic monitor 200, which can be removed from the user's body during showers, exercise, sleep or the like. In addition, the use of multiple components (e.g., transmitter 100 and characteristic monitor 200) facilitates upgrades or replacements, since one module or the other can be modified or replaced without requiring complete replacement of the monitor system 1. Further, the use of multiple components can improve the economics of manufacturing, since some components may require replacement on a more frequent basis, sizing requirements may be different for each module, there may be different assembly environment requirements, and modifications can be made without affecting the other components.

The telemetered characteristic monitor transmitter 100 takes characteristic information, such as glucose data or the like, from the percutaneous sensor set 10 and transmits it via wireless telemetry to the characteristic monitor 200, which displays and logs the received glucose readings. Logged data can be downloaded from the characteristic monitor 200 to a personal computer, laptop, or the like, for detailed data analysis. In further embodiments, the telemetered characteristic monitor system 1 may be used in a hospital environment or the like. Still further embodiments of the present invention may include one or more buttons (on the telemetered characteristic monitor transmitter 100 or characteristic monitor 200 ) to record data and events for later analysis, correlation, or the like. In addition, the telemetered characteristic monitor transmitter 100 may include a transmit on/off button for compliance with safety standards and regulations to temporarily suspend transmissions. Further buttons can include a sensor on/off button to conserve power and to assist in initializing the sensor set 10. The telemetered characteristic monitor transmitter 100 and characteristic monitor 200 may also be combined with other medical devices to combine other patient data through a common data network and telemetry system.

Further embodiments of the percutaneous sensor set 10 would monitor the temperature of the sensor set 10, which can then be used to improve the calibration of the sensor. For instance, for a glucose sensor, the enzyme reaction activity may have a known temperature coefficient. The relationship between temperature and enzyme activity can be used to adjust the sensor values to more accurately reflect the actual characteristic levels. In addition to temperature measurements, the oxygen saturation level can be determined by measuring signals from the various electrodes of the sensor set 10. Once obtained, the oxygen saturation level may be used in calibration of the sensor set 10 due to changes in the oxygen saturation levels, and its effects on the chemical reactions in the sensor set 10. For instance, as the oxygen level goes lower the sensor sensitivity may be lowered. The oxygen level can be utilized in calibration of the sensor set 10 by adjusting for the changing oxygen saturation. In alternative embodiments, temperature measurements may be used in conjunction with other readings to determine the required sensor calibration.

As shown in FIGS. 1–7, a percutaneous sensor set 10 is provided for subcutaneous placement of an active portion of a flexible sensor 12 (see FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. After insertion, the insertion needle 14 is withdrawn to leave the cannula 16 with the sensing portion 18 and the sensor electrodes 20 in place at the selected insertion site.

In preferred embodiments, the percutaneous sensor set 10 facilitates accurate placement of a flexible thin film electrochemical sensor 12 of the type used for monitoring specific blood parameters representative of a user's condition. Preferably, the sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

Preferred embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 (see FIG. 2) that terminates in conductive contact pads, or the like, which are also exposed through one of the insulative layers. In alternative embodiments, other types of implantable sensors, such as chemical based, optical based, or the like, may be used.

As is known in the art, and illustrated schematically in FIG. 2, the connection portion 24 and the contact pads are generally adapted for a direct wired electrical connection to a suitable monitor 200 for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the monitor 200 or a telemetered characteristic monitor transmitter 100 by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 are configured or formed to work with either a wired or a wireless characteristic monitor system.

The proximal part of the sensor 12 is mounted in a mounting base 30 adapted for placement onto the skin of a user. As shown, the mounting base 30 is a pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In the illustrated embodiment, the mounting base is generally rectangular, but alternative embodiments may be other shapes, such as circular, oval, hour-glass, butterfly, irregular, or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a full round cross-sectional shape, and may be closed off at a rear end of the needle 14. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled 'DISPOSABLE SENSOR INSERTION ASSEMBLY," which are herein incorporated by reference.

Figure 6:
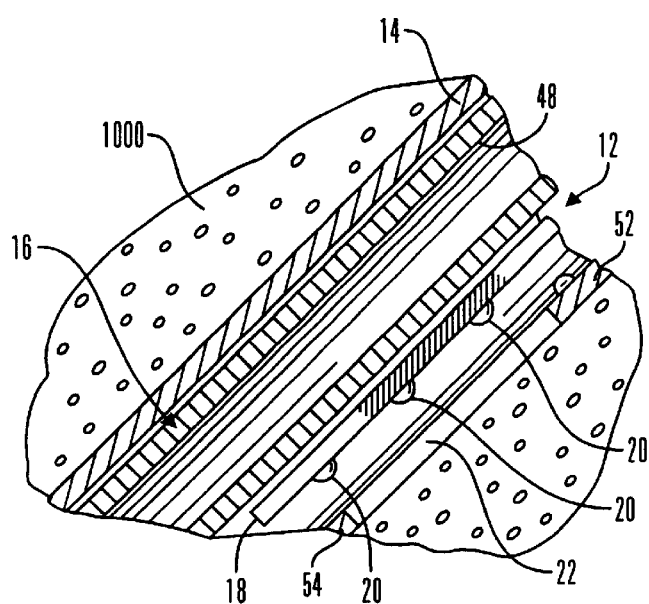
FIG. 6 is an enlarged fragmented sectional view corresponding generally with the encircled region 6 of FIG. 2.
Figure 7:
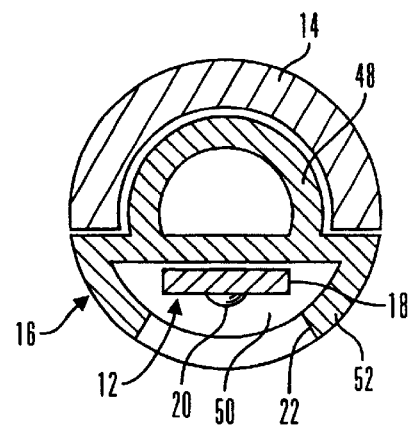
FIG. 7 is an enlarged transverse section taken generally on the line 7-7 of FIG. 2.

The cannula 16 is best shown in FIGS. 6 and 7, and includes a first portion 48 having partly-circular cross-section to fit within the insertion needle 14 that extends downwardly from the mounting base 30. In alternative embodiments, the first portion 48 may be formed with a solid core; rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guideably supporting the sensing portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed. Alternatively, a membrane can cover this area with a porosity that controls rapid diffusion of glucose through the membrane.

Figure 8A:
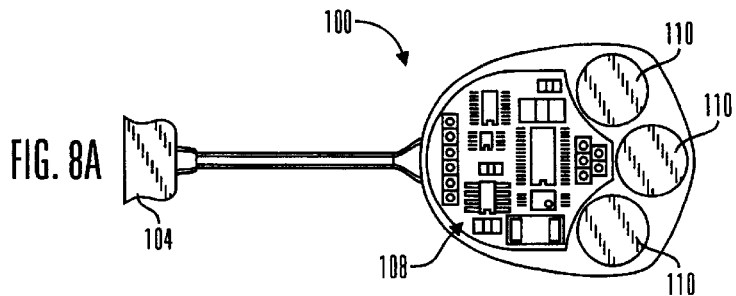
FIG. 8(a) is a top plan and partial cut-away view of the telemetered characteristic monitor transmitter device in accordance with the embodiment shown in FIG. 1.

As shown in FIGS. 1, 2 and 8(a), the telemetered characteristic monitor transmitter 100 is coupled to a sensor set 10 by a cable 102 through a connector 104 that is electrically coupled to the connector block 28 of the connector portion 24 of the sensor set 10. In alternative embodiments, the cable 102 may be omitted, and the telemetered characteristic monitor transmitter 100 may include an appropriate connector (not shown) for direct connection to the connector portion 24 of the sensor set 10 or the sensor set 10 may be modified to have the connector portion 24 positioned at a different location, such as for example, on the top of the sensor set 10 to facilitate placement of the telemetered characteristic monitor transmitter over the subcutaneous sensor set 10. This would minimize the amount of skin surface covered or contacted by medical devices, and tend to minimize movement of the sensor set 10 relative to the telemetered characteristic monitor transmitter 100. In further alternative embodiments, the cable 102 and the connector 104 may be formed as add-on adapters to fit different types of connectors on different types or kinds of sensor sets. The use of adapters would facilitate adaptation of the telemetered characteristic monitor transmitter 100 to work with a wide variety of sensor systems. In further embodiments, the telemetered characteristic monitor transmitter 100 may omit the cable 102 and connector 104 and is instead optically couple with an implanted sensor, in the subcutaneous, dermal, sub-dermal, inter-peritoneal or peritoneal tissue, to interrogate the implanted sensor using visible, and/or IR frequencies, either transmitting to and receiving a signal from the implanted sensor or receiving a signal from the implanted sensor.

The telemetered characteristic monitor 100 (also known as Potentiostat Transmitter Device) includes a housing 106 that supports a printed circuit board 108, batteries 110, antenna 112, and the cable 102 with the connector 104. In preferred embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In preferred embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. In preferred embodiments, the housing 106 is disk or oval shaped. However, in alternative embodiments, other shapes, such as hour glass, rectangular or the like, may be used. Preferred embodiments of the housing 106 are sized in the range of 2.0 square inches by 0.35 inches thick to minimize weight, discomfort and the noticeability of the telemetered characteristic monitor transmitter 100 on the body of the user. However, larger or smaller sizes, such as 1.0 square inches and 0.25 inches thick or less, and 3.0 square inches and 0.5 inches thick or more, may be used. Also, the housing may simply be formed from potted epoxy, or other material, especially if the battery life relative to the device cost is long enough, or if the device is rechargeable.

As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use. In preferred embodiments, the adhesive layer 118 includes an anti-bacterial agent to reduce the chance of infection; however, alternative embodiments may omit the agent. In further alternative embodiments, the adhesive layer 118 may be omitted and the telemetered characteristic monitor transmitter 100 is secured to the body by other methods, such as an adhesive overdressing, straps, belts, clips or the like.

In preferred embodiments, the cable 102 and connector 104 are similar to (but not necessarily identical to) shortened versions of a cable and connector that are used to provide a standard wired connection between the sensor set 10 and the characteristic monitor 200. This allows the telemetered characteristic monitor transmitter 100 to be used with existing sensor sets 10, and avoids the necessity to re-certify the connector portion 24 of the sensor set 10 for use with a wireless connection. The cable 102 should also include a flexible strain relief portion (not shown) to minimize strain on the sensor set 10 and prevent movement of the inserted sensor 12, which can lead to discomfort or dislodging of the sensor set 10. The flexible strain relief portion is intended to minimize sensor artifacts generated by user movements that might cause the sensing area of the sensor set 10 to move relative to the body tissues in contact with the sensing area of the sensor set 10.

Figure 8B:
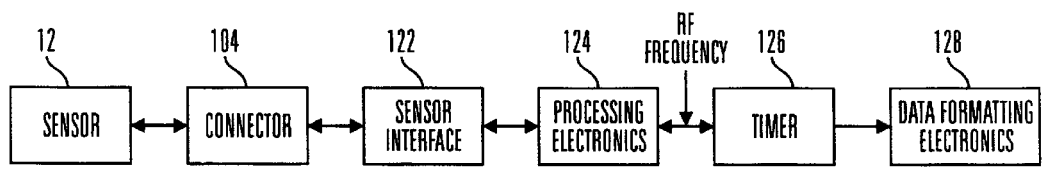
FIG. 8(b) is a simplified block diagram of the printed circuit board of the telemetered characteristic monitor transmitter device in accordance with the embodiments shown in FIG. 1.

The printed circuit board 108 of the telemetered characteristic monitor transmitter 100 includes a sensor interface 122, processing electronics 124, timers 126, and data formatting electronics 128, as shown in FIG. 8(b). In preferred embodiments, the sensor interface 122, processing electronics 124, timers 126, and data formatting electronics 128 are formed as separate semiconductor chips; however, alternative embodiments may combine the various semiconductor chips into a single customized semiconductor chip. The sensor interface 122 connects with the cable 102 that is connected with the sensor set 10. In preferred embodiments, the sensor interface is permanently connected to the cable 102. However, in alternative embodiments, the sensor interface 122 may be configured in the form of a jack to accept different types of cables that provide adaptability of the telemetered characteristic monitor transmitter 100 to work with different types of sensors and/or sensors placed in different locations of the user's body. In preferred embodiments, the printed circuit board 108, and associated electronics, are capable of operating in a temperature range of 0° C. and 50° C. However, larger or smaller temperature ranges may be used.

Preferably, the battery assembly will use a weld tab design to connect power to the system. For example, it can use three series silver oxide 357 battery cells 110, or the like. However, it is understood that different battery chemistries may be used, such as lithium based chemistries, alkaline batteries, nickel metalhydride, or the like, and different numbers of batteries can be used. In further embodiments, the sensor interface 122 will include circuitry and/or a mechanism for detecting connection to the sensor set 10. This would provide the capability to save power and to more quickly and efficiently start initialization of the sensor set 10. In preferred embodiments, the batteries 110 have a life in the range of 3 months to 2 years, and provide a low battery warning alarm. Alternative embodiments may provide longer or shorter battery lifetimes, or include a power port, solar cells or an inductive coil to permit recharging of rechargeable batteries in the telemetered characteristic monitor transmitter 100.

In preferred embodiments, the telemetered characteristic monitor transmitter 100 provides power, through the cable 102 and cable connector 104 to the sensor set 10. The power is used to monitor and drive the sensor set 10. The power connection is also used to speed the initialization of the sensor 12, when it is first placed under the skin. The use of an initialization process can reduce the time for sensor 12 stabilization from several hours to an hour or less. The preferred initialization procedure uses a two step process. First, a high voltage (preferably between 1.0–1.2 volts—although other voltages may be used) is applied to the sensor 12 for 1 to 2 minutes (although different time periods may be used) to allow the sensor 12 to stabilize. Then, a lower voltage (preferably between 0.5–0.6 volts—although other voltages may be used) is applied for the remainder of the initialization process (typically 58 minutes or less). Other stabilization/initialization procedures using differing currents, currents and voltages, different numbers of steps, or the like, may be used. Other embodiments may omit the initialization/stabilization process, if not required by the sensor or if timing is not a factor.

At the completion of the stabilizing process, a reading may be transmitted from the sensor set 10 and the telemetered characteristic monitor transmitter 100 to the characteristic monitor 200, and then the user will input a calibrating glucose reading into characteristic monitor 200. In alternative embodiments, a fluid containing a known value of glucose may be injected into the site around the sensor set 10, and then the reading is sent to the characteristic monitor 200 and the user inputs the known concentration value, presses a button (not shown) or otherwise instructs the monitor to calibrate using the known value. During the calibration process, the telemetered characteristic monitor transmitter 100 checks to determine if the sensor set 10 is still connected. If the sensor set 10 is no longer connected, the telemetered characteristic monitor transmitter 100 will abort the stabilization process and sound an alarm (or send a signal to the characteristic monitor 200 to sound an alarm).

Figure 9:
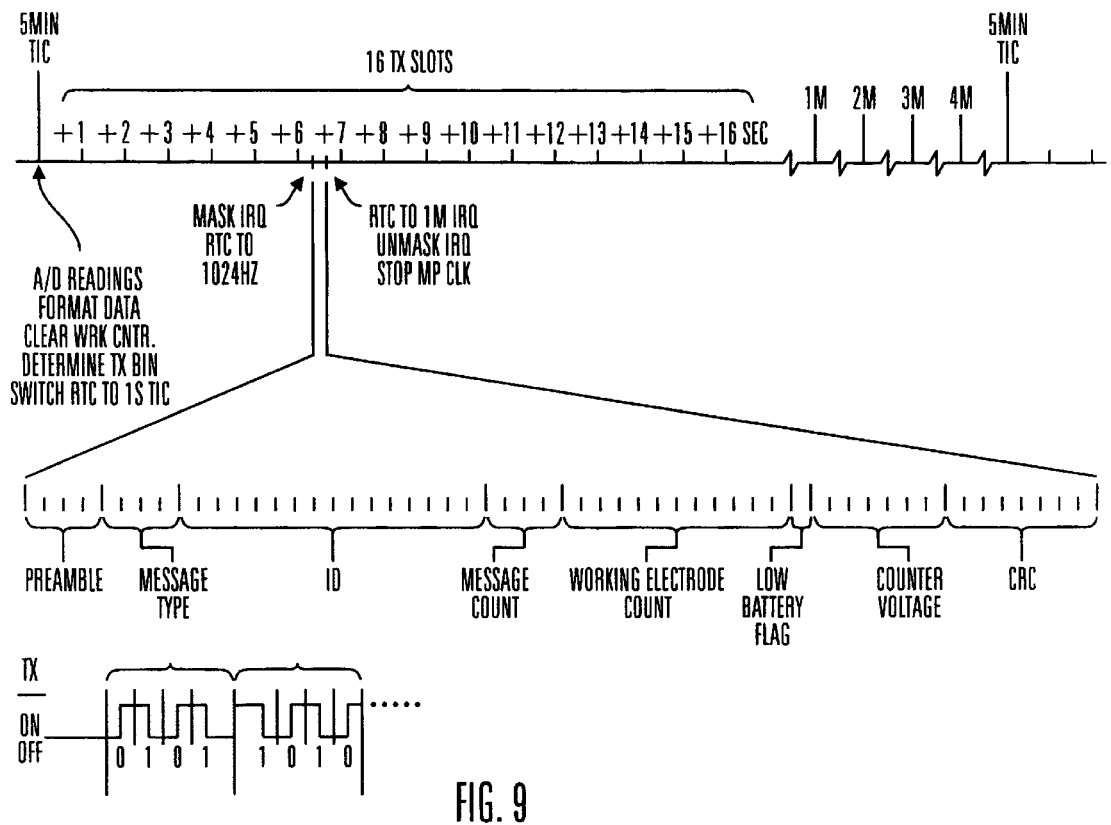
FIG. 9 is a timing diagram illustrating an embodiment of a message and timing format used by the telemetered characteristic monitor transmitter device shown in FIG. 1.

Preferably, the transmissions (or telemetry) of the telemetered characteristic monitor transmitter 100 will contain at least the following information: a unique ID code that uniquely identifies each telemetered characteristic monitor transmitter 100, a sensor characteristic data signal representative of the measured characteristic value (e.g., glucose or the like) from the sensor 18 of the subcutaneous sensor set 10, a counter electrode voltage, a low battery flag, and error detection bits (such as CRC). FIG. 9 and Table 1 illustrate a preferred message format for the telemetry of the telemetered characteristic monitor transmitter 100. However, it will be understood that different message protocols and structures may be used.

TABLE 1

Message format

1. Encoding method: OOK MANCHESTER
   (1 = 1/0, 0 = 0/1 sequence, where 1 = transmitter (TX) on)
2. Clock rate 1024 Hz (512 Hz symbol/bit rate).
3. Message format:
   Preamble: 4 bits (0101, want only one transition per bit)
   Message Type: 4 bits (1010 = transmitter 100,
   15 others for pump/ppc protocol)
   Unique ID #: 16 bits (65536 unique numbers)
   Message count #: 4 bits (also determines TX time slot)
   Working 12 bits (9 MSBs + 3 magnitude bits =

TABLE 1-continued

Message format

| | |
|---|---|
| Electrode: | 16 bit range - converted by the characteristic monitor 200 into a value representative of characteristic level, such as glucose level) |
| Low battery flag: | 1 bit (0 = ok, 1 = low) |
| Counter Voltage: | 7 bits (0–1.2 V typ., 8 bit a/d 3.2 V FS) |
| CRC: | 8 bits |
| Total | 56 bits (×1/512 hz = 109 mS) |

4. Message TX interval: 300 seconds (5 min) + 1–16 seconds pseudo-random delay (TX time slot)
5. TX duty cycle: 56 bits*1/512 Hz*1/300 S*½ = 1.823e-4

Preferred embodiments utilize a time-slicing transmission protocol. Use of the time slicing protocol facilitates the use of multiple signals on the same frequency bands or to the same receiver from multiple transmitters. The time-slicing may also be used to obviate the need for a receiver in the telemetered characteristic monitor transmitter 100. For instance, the use of intermittent transmission reduces the amount of power required to operate the transmitter 100 and to extend the life of the device. It also saves power in the characteristic monitor 200 by reducing the amount of time the characteristic monitor 200 must spend in the receive mode.

In preferred embodiments, when the telemetered characteristic monitor transmitter 100 is connected to the sensor set 10, it detects the connection and is activated. Next, if desired or necessary, the telemetered characteristic monitor transmitter 100 initializes the sensor 12 of the sensor set 10. After (or in some cases during) initialization, the telemetered characteristic monitor transmitter 100 sends out a message of between 100–150 ms length every 5 minutes. Although other timing intervals ranging from 1 second to 30 minutes may be used.

Preferably, the message is transmitted in a pseudo-randomly selected time window within the 128 seconds following the 5 minute interval. In preferred embodiments, the telemetered characteristic transmitter 100 utilizes its own unique ID as a random-seed to set up a table of transmission time windows that defines the order in which the telemetered characteristic monitor 100 will transmit a message following the 5 minute interval. The order is repeated after the table is set-up. Included in the message sent will be the message count number, which indicates where in the sequence of time windows the telemetered characteristic monitor transmitter is currently transmitting. The characteristic monitor 200 uses the unique ID code of the telemetered characteristic monitor transmitter 100 to set up a corresponding table in the characteristic monitor 200 and the received message count to synchronize the characteristic monitor 200 with the current position in the table being used by the telemetered characteristic monitor transmitter 100 to predict the next time window to be used. The use of pseudo-random time windows prevents multiple transmitters from continuously interfering with other transmitting devices that are temporarily, or inadvertently, synchronized with the telemetered characteristic monitor transmitter 100. The characteristic monitor 200 acquires the transmitted message, and determines the time window in which the characteristic monitor 200 must be in a receive mode to acquire the next message. The characteristic monitor 200 then places itself in the receive mode every 5 minutes (although other timing intervals from 1 second to 30 minutes may be used) to receive the next message and data from the telemetered characteristic monitor transmitter 100 at the next predicted time window. Thus, the characteristic monitor 200 needs only be in the receive mode for 1 second (i.e., 1 time window); rather than 128 seconds (128 time windows). In alternative embodiments, the characteristic monitor 200 may not use the unique ID and the message count and may remain in the receive mode during the entire period (e.g., for 128 time windows) during which a transmission is possible. In addition, other embodiments may cause the characteristic monitor 200 to enter the receive mode 1 time window ahead and stay on for 1 time window longer to maximize the likelihood of receiving the next transmission. In further alternative embodiments, the telemetered characteristic monitor transmitter 100 and/or characteristic monitor 200 may utilize other methods or numbers to determine when transmission time windows are selected. Alternative message time-slicing transmission parameters, such as message length, number of time windows, frequency of transmissions, or the like, that are larger or smaller then those describe above, may also be used. Preferred embodiments transmit the data and/or information at a data rate between 1000 Hz to 4000 Hz modulated onto a high frequency carrier wave. However, alternative embodiments may use smaller or larger transmission rates, with the rate being selected based on user environment, power requirements, interference issues, redundancy criteria, or the like.

If a transmitted message is not received by the characteristic monitor 200 after a predetermined period of time, an alarm will be sounded or provided. In addition, the characteristic monitor 200 may continue to attempt to receive the next message by entering the receive mode at the next anticipated transmission time or may expand to enter the receive mode to cover all time windows until the next message is received.

In another alternative embodiment, if there is little or no likelihood of interference from other telemetered characteristic monitor transmitter 100, such as by message length, frequency selections or the like, the telemetered characteristic monitor transmitter 100 may transmit at one time window for all cases (typically the choice of window may be randomly selected at connection of a sensor set 10 or set at the factory). This permits the characteristic monitor 200 to be in the receive mode for even shorter periods of time (i.e., approximately 200 ms to bracket the telemetered characteristic monitor transmitter 100 transmission instead of the 128 seconds (or 1 second if able to predict the next time window) needed to bracket 128 windows) to conserve power in the characteristic monitor 200. For instance, in this scenario, the characteristic monitor 200 will be in a non-receive mode for 299.8 seconds and in a receive mode for 200 ms. In particular embodiments the non-receive mode and receive mode periods will be determined by the message length and expected frequency of transmission. It is also noted that in a system where the receiver must cover a range of time windows, the receiver may lock on to a particular range of time windows to permit the receiver being in the receive mode for shorter periods of time.

The use of these transmission protocols obviates the need for a transmitter and receiver in both the telemetered characteristic monitor transmitter 100 and characteristic monitor 200, which reduces costs, simplifies the system design, reduces power consumption and the like. However, alternative embodiments may include the capability for two-way communication, if desirable. In further embodiments, the telemetered characteristic monitor transmitter 100 transmits continuously and the characteristic monitor 200 enters the receive mode when desired or required to determine a characteristic value, such as a glucose level or the like.

In preferred embodiments, the telemetered characteristic monitor transmitter 100 will have the ability to uniquely identify itself to the characteristic monitor 200. The telemetered characteristic monitor transmitter 100 will have an operating range to the characteristic monitor 200 of at least 10 feet. In alternative embodiments, larger or smaller ranges may be used, with the selection being dependent on the environment in which the telemetered characteristic monitor transmitter 100 will be used, the size and needs of the user, power requirements, and the like.

In further alternative embodiments, the telemetered characteristic monitor transmitter 100 can be combined with a sensor set 10 as a single unit. This would be particularly well adapted where batteries and the transmitter can be made cheaply enough to facilitate changing the transmitter 100 with each new sensor set 10.

Figure 10:
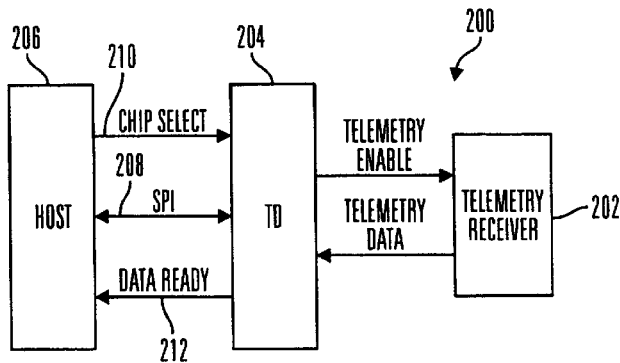
FIG. 10 is a simplified block diagram of a characteristic monitor used in accordance with an embodiment of the present invention.

As shown in FIG. 10, the characteristic monitor 200 includes a telemetry receiver 202, a Telemetry Decoder (TD) 204 and a host micro-controller (Host) 206 for communication with the telemetered characteristic monitor transmitter 100. The TD 204 is used to decode a received telemetry signal from the transmitter device and forward the decoded signal to the Host 206. The Host 206 is a microprocessor for data reduction, data storage, user interface, or the like. The telemetry receiver 202 receives the characteristic data (e.g., glucose data) from the telemetered characteristic monitor transmitter, and passes it to the TD 204 for decoding and formatting. After complete receipt of the data by the TD 204, the data is transferred to the Host 206 for processing, where calibration information, based upon user entered characteristic readings (e.g., blood glucose readings), is performed to determine the corresponding characteristic level (e.g., glucose level) from measurement in the characteristic data (e.g., glucose data). The Host 206 also provides for storage of historical characteristic data, and can download the data to a personal computer, lap-top, or the like, via a com-station, wireless connection, modem or the like. For example, in preferred embodiments, the counter electrode voltage is included in the message from the telemetered characteristic monitor transmitter 100 and is used as a diagnostic signal. The raw current signal values generally range from 0 to 999, which represents sensor electrode current in the range between 0.0 to 99.9 nanoAmperes, and is converted to characteristic values, such as glucose values in the range of 40 to 400 mg/dl. However, in alternative embodiments, larger or smaller ranges may be used. The values are then displayed on the characteristic monitor 200 or stored in data memory for later recall.

The characteristic monitor 200 also includes circuitry in the TD 204 to uniquely mate it to an identified telemetered characteristic monitor transmitter 100. In preferred embodiments, the identification number of the telemetered characteristic monitor transmitter 100 is entered manually by the user using keys located on the characteristic monitor 200. In alternative embodiments, the characteristic monitor 200 includes a "learn ID" mode. Generally, the "learn ID" mode is best suited for the home environment, since multiple telemetered characteristic monitor transmitters 100, typically encountered in a hospital setting, are less likely to cause confusion in the characteristic monitor 200 when it attempts to learn an ID code. In addition, the characteristic monitor 200 will include the ability to learn or be reprogrammed to work with a different (or replacement) telemetered characteristic monitor transmitter 100. The preferred operating distance is at least 10 feet. In alternative embodiments, larger or smaller ranges may be used, with the selection being dependent on the environment in which the telemetered characteristic monitor transmitter 100 will be used, the size and needs of the user, power requirements, and the like. Furthermore, if the characteristic monitor 200 does not receive a transmission from the identified telemetered characteristic monitor transmitter 100 after a certain period of time (e.g., one or more missed transmissions), an alarm will be sounded.

Figure 11:
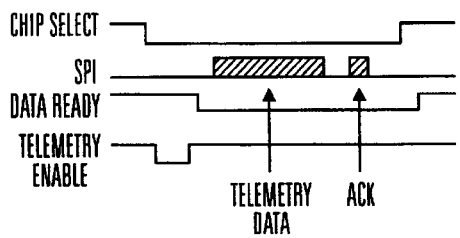
FIG. 11 is a timing diagram for the characteristic monitor shown in FIG. 10.
Figure 12:
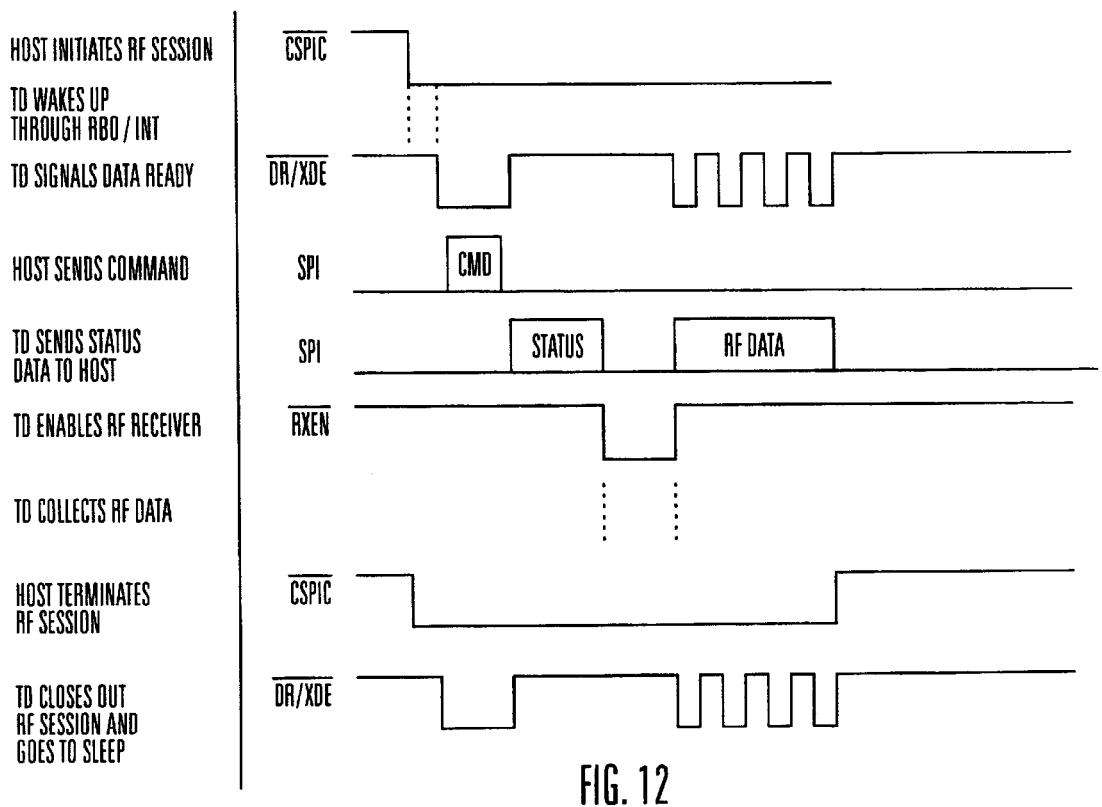
FIG. 12 is another timing diagram for the characteristic monitor shown in FIG. 10.

In preferred embodiments, the characteristic monitor 200 utilizes a two processor system, in which the Host 206 is the master processor and the TD 204 is a slave processor dedicated to telemetry processing. A first communication protocol between the Host 206 and the TD 204 is shown in FIG. 11. The first protocol uses a serial peripheral interface (SPI) 208 and two control lines 210 and 212; one control line (chip select—CSPIC) 210 is used by Host 206 to wake up the TD 204 to initiate telemetry receiving task; and the other control line (data ready—DR) 212 is used by the TD 204 to indicate to the Host 206 that the telemetry data from the telemetered characteristic monitor transmitter has been received and is ready to be transferred to the HC08 206. Upon receiving data through the SPI 208, the Host 206 sends an acknowledgment through the SPI 208 to the TD 204. In preferred embodiments, fixed length data blocks are used. However, in alternative embodiments, variable length data blocks may be used. In preferred embodiments, the Host 206 may pull the Chip Select (CSPIC) 210 high at any time to abort the telemetry data transfer from the TD 204. Alternatively, an additional line (not shown) may be used to reset the TD 204. FIG. 12 shows a second, more complex, alternative protocol that is used by the Host 206 and the TD 204.

In alternative embodiments, the TD 204 and Host 206 may be combined together in a single semiconductor chip to obviate the need for dual processors and to reduce the space needed for the electronics. In further embodiments, the functions of the TD 204 and Host 206 may be allocated differently between one or more processors.

As shown in FIG. 2, the characteristic monitor may include a display 214 that is used to display the results of the measurement received from the sensor 18 in the sensor set 10 via the telemetered characteristic monitor transmitter 100. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 214 may also be used with buttons (not shown) on the characteristic monitor to program or update data in the characteristic monitor 200. It is noted that the typical user can be expected to have somewhat diminished visual and tactile abilities due to complications from diabetes or other conditions. Thus, the display 214 and buttons should be configured and adapted to the needs of a user with diminished visual and tactile abilities. In alternative embodiments, the value can be conveyed to the user by audio signals, such as beeps, speech or the like. Still further embodiments may use a touch screen instead of (or in some cases addition to) buttons to facilitate water proofing and to ease changes in the characteristic monitor 200 hardware to accommodate improvements or upgrades.

Preferably, the characteristic monitor uses batteries (not shown) to provide power to the characteristic monitor. For example, a plurality of silver oxide batteries may be used.

However, it is understood that different battery chemistries may be used, such as lithium based, alkaline based, nickel metalhydride, or the like, and different numbers of batteries can be used. In preferred embodiments, the batteries have a life in the range of 1 month to 2 years, and provide a low battery warning alarm. Alternative embodiments may provide longer or shorter battery lifetimes, or include a power port, solar cells or an induction coil to permit recharging of rechargeable batteries in the characteristic monitor 200. In preferred embodiments, the batteries are not replaceable to facilitate waterproofing the housing 106.

In further embodiments of the present invention, the characteristic monitor 200 may be replaced by a different device. For example, in one embodiment, the telemetered characteristic monitor transmitter 100 communicates with an RF programmer (not shown) that is also used to program and obtain data from an infusion pump or the like. The RF programmer may also be used to update and program the transmitter 100, if the transmitter 100 includes a receiver for remote programming, calibration or data receipt. The RF programmer can be used to store data obtained from the sensor 18 and then provide it to either an infusion pump, characteristic monitor, computer or the like for analysis. In further embodiments, the transmitter 100 may transmit the data to a medication delivery device, such as an infusion pump or the like, as part of a closed loop system. This would allow the medication delivery device to compare sensor results with medication delivery data and either sound alarms when appropriate or suggest corrections to the medication delivery regimen. In preferred embodiments, the transmitter 100 would include a transmitter to receive updates or requests for additional sensor data. An example of one type of RF programmer can be found in U.S. patent application Ser. No. 60/096,994 filed Aug. 18, 1998 and is entitled "INFUSION DEVICE WITH REMOTE PROGRAMMING, CARBOHYDRATE CALCULATOR AND/OR VIBRATION ALARM CAPABILITIES," or U.S. patent application Ser. No. 09/334,858 filed Jun. 17, 1999 and is entitled "EXTERNAL INFUSION DEVICE WITH REMOTE PROGRAMMING, BOLUS ESTIMATOR AND/OR VIBRATION ALARM CAPABILITIES," both of which are herein incorporated by reference.

In further embodiments, the telemetered characteristic monitor transmitter can include a modem, or the like, to transfer data to and from a healthcare professional. Further embodiments, can receive updated programming or instructions via a modem connection.

In use, the sensor set 10 permits quick and easy subcutaneous placement of the active sensing portion 18 at a selected site within the body of the user. More specifically, the peel-off strip 34 (see FIG. 1) is removed from the mounting base 30, at which time the mounting base 30 can be pressed onto and seated upon the patient's skin. During this step, the insertion needle 14 pierces the user's skin and carries the protective cannula 16 with the sensing portion 18 to the appropriate subcutaneous placement site. During insertion, the cannula 16 provides a stable support and guide structure to carry the flexible sensor 12 to the desired placement site. When the sensor 12 is subcutaneously placed, with the mounting base 30 seated upon the user's skin, the insertion needle 14 can be slidably withdrawn from the user. During this withdrawal step, the insertion needle 14 slides over the first portion 48 of the protective cannula 16, leaving the sensing portion 18 with electrodes 20 directly exposed to the user's body fluids via the window 22. Further description of the needle 14 and the sensor set 10 are found in U.S. Pat. No. 5,586,553, entitled "TRANSCUTANEOUS SENSOR INSERTION SET"; co-pending U.S. patent application Ser. No. 08/871,831, entitled 'DISPOSABLE SENSOR INSERTION ASSEMBLY"; and co-pending U.S. patent application Ser. No. 09/161,128, filed Sep. 25, 1998, entitled "A SUBCUTANEOUS IMPLANTABLE SENSOR SET HAVING THE CAPABILITY TO REMOVE OR DELIVER FLUIDS TO AN INSERTION SITE," which are herein incorporated by reference.

Next, the user connects the connection portion 24 of the sensor set 10 to the cable 102 of the telemetered characteristic monitor transmitter 100, so that the sensor 12 can then be used over a prolonged period of time for taking blood chemistry or other characteristic readings, such as blood glucose readings in a diabetic patient. Preferred embodiments of the telemetered characteristic monitor transmitter 100 detect the connection of the sensor 12 to activate the telemetered characteristic monitor transmitter 100. For instance, connection of the sensor 12 may activate a switch or close a circuit to turn the telemetered characteristic monitor transmitter 100 on. The use of a connection detection provides the capability to maximize the battery and shelf life of the telemetered characteristic monitor transmitter prior to use, such as during manufacturing, test and storage. Alternative embodiments of the present invention may utilize an on/off switch (or button) on the telemetered characteristic monitor transmitter 100.

The transmitter 100 is then affixed to the user's body with an adhesive overdressing. Alternatively, the peel-off strip 34 (see FIG. 1) is removed from the lower case 116, at which time the lower case 116 can be pressed onto and seated upon the patient's skin. The user then activates the transmitter 100, or the transmitter is activated by detection of the connection to the sensor 12 of the sensor set 10. Generally, the act of connecting (and disconnecting) the sensor 12 activates (and deactivates) the telemetered characteristic monitor 100, and no other interface is required. In alternative steps, the sensor set 10 is connected to the transmitter 100 prior to placement of the sensor 12 to avoid possible movement or dislodging of the sensor 12 during attachment of the transmitter 100. Also, the transmitter may be attached to the user prior to attaching the sensor set 10 to the transmitter 100.

The user then programs the characteristic monitor (or it learns) the identification of the transmitter 100 and verifies proper operation and calibration of the transmitter 100. The characteristic monitor 200 and transmitter 100 then work to transmit and receive sensor data to determine characteristic levels. Thus, once a user attaches a transmitter 100 to a sensor set 10, the sensor 12 is automatically initialized and readings are periodically transmitted, together with other information, to the characteristic monitor 200.

After a sensor set 10 has been used for a period of time, it is replaced. The user will disconnect the sensor set 10 from the cable 102 of the telemetered characteristic monitor transmitter 100. In preferred embodiments, the telemetered characteristic monitor transmitter 100 is removed and posited adjacent the new site for a new sensor set 10. In alternative embodiments, the user does not need to remove the transmitter 100. A new sensor set 10 and sensor 12 are attached to the transmitter 100 and connected to the user's body. Monitoring then continues, as with the previous sensor 12. If the user must replace the telemetered characteristic monitor transmitter 100, the user disconnects the transmitter 100 from the sensor set 10 and the user's body. The user then connects a new transmitter 100, and reprograms the characteristic monitor (or learns) to work with the new transmitter 100. Monitoring then continues, as with the previous sensor 12.

Additional embodiments of the present invention may include a vibrator alarm (or optional indicator such as an L.E.D.) in either or both the telemetered characteristic monitor transmitter 100 and the characteristic monitor 200 to provide a tactile (vibration) alarm to the user, such as sensor set malfunction, improper connection, low battery, missed message, bad data, transmitter interference, or the like. The use of a vibration alarm provides additional reminders to an audio alarm, which could be important with someone suffering an acute reaction, or to have non-audio alarms to preserve and conceal the presence of the telemetered characteristic monitor system 1.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An external telemetered characteristic monitor transmitter device for use in a system with a remotely located characteristic monitor and a sensor producing a signal indicative of a characteristic of a user, the transmitter device comprising:

a housing;

a sensor connector coupled to the housing and that is connectable to the sensor outside a body of the user to receive the signal from the sensor;

a processor within the housing coupled to the sensor connector to process the signal from the sensor for delivery to the remotely located characteristic monitor; and a transmitter coupled to the processor for wirelessly transmitting the processed signals to the remotely located characteristic monitor worn on a body of the user and concealable within clothing, wherein the remotely located characteristic monitor utilizes the received processed signals to determine a display a characteristic reading of the user, wherein the transmitter device has a unique ID code and the transmitter transmits the processed signals to the remotely located characteristic monitor in pseudo-randomly selected time windows based on the unique ID code of the transmitter such that the transmitter is synchronized with the remotely located characteristic monitor.

2. The external telemetered characteristic monitor transmitter device according to claim 1, wherein the pseudo-randomly selected time windows are established by utilizing the unique ID code of the transmitter to set up a table of transmission time windows that defines an order in which the transmitter will transmit the message.

3. The external telemetered characteristic monitor transmitter device according to claim 2, wherein the order is repeated after the table is set up.

4. The external telemetered characteristic monitor transmitter device according to claim 2, wherein the message includes a message count number which indicates where in the sequence of time windows the transmitter is currently transmitting.

5. The external telemetered characteristic monitor transmitter device according to claim 1, wherein the pseudo-randomly selected time window is one second.

* * * * *